United States Patent
Luesch

(10) Patent No.: US 9,181,304 B2
(45) Date of Patent: Nov. 10, 2015

(54) MACROCYCLIC THERAPEUTIC AGENTS AND METHODS OF TREATMENT

(75) Inventor: Hendrik Luesch, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 14/118,513

(22) PCT Filed: May 17, 2012

(86) PCT No.: PCT/US2012/038374
§ 371 (c)(1),
(2), (4) Date: Nov. 18, 2013

(87) PCT Pub. No.: WO2012/158933
PCT Pub. Date: Nov. 22, 2012

(65) Prior Publication Data
US 2014/0088016 A1    Mar. 27, 2014

Related U.S. Application Data

(60) Provisional application No. 61/487,583, filed on May 18, 2011.

(51) Int. Cl.
| | |
|---|---|
| *A61K 38/00* | (2006.01) |
| *C07K 14/78* | (2006.01) |
| *C07K 11/02* | (2006.01) |
| *C07D 498/08* | (2006.01) |
| *C07D 498/18* | (2006.01) |
| *C07D 513/08* | (2006.01) |
| *C07D 513/18* | (2006.01) |
| *A61K 38/15* | (2006.01) |
| *A61K 45/06* | (2006.01) |

(52) U.S. Cl.
CPC ............... *C07K 11/02* (2013.01); *A61K 38/15* (2013.01); *A61K 45/06* (2013.01); *C07D 498/08* (2013.01); *C07D 498/18* (2013.01); *C07D 513/08* (2013.01); *C07D 513/18* (2013.01)

(58) Field of Classification Search
CPC ......... A61K 38/15; A61K 51/08; C07K 11/02
See application file for complete search history.

(56) References Cited

FOREIGN PATENT DOCUMENTS

| WO | WO-2009032338 A1 | 3/2009 |
| WO | WO-2009032351 A1 | 3/2009 |
| WO | WO-2010065563 A2 | 6/2010 |

OTHER PUBLICATIONS

Luesch, H. et al., New Apratoxins of Marine Cyanobacterial Origin from Guam and Palau.; Bioorganic & Medicinal Chemistry. 2002, vol. 10, pp. 1973-1978.
Chen, Qi-Yin et. al., Systematic Chemical Mutagenesis Identifies a Potent Novel Apratoxin A/E Hybrid with Improved in Vivo Antitumor Activity. ACS Medicinal Chemistry Letters. Nov. 10, 2011, vol. 2, No. 11, pp. 861-865.
International Search Report for PCT/US2012/038374.

*Primary Examiner* — Marcela M Cordero Garcia
*Assistant Examiner* — Kaipeen Yang
(74) *Attorney, Agent, or Firm* — Locke Lord LLP; Jeffrey D. Hsi; Stephen W. Rafferty

(57) ABSTRACT

The instant invention describes macrocyclic compounds having therapeutic activity, and the mechanism and methods of treating disorders such as autoimmune diseases, inflammation, and cancer, tumors and cell proliferation related disorders.

3 Claims, No Drawings

MACROCYCLIC THERAPEUTIC AGENTS AND METHODS OF TREATMENT

CROSS-REFERENCE TO RELATED APPLICATIONS

This application is the U.S. National Stage, pursuant to 35 U.S.C. §371, of U.S. International Application No. PCT/US2012/038374, filed May 17, 2012, designating the United States, which claims the benefit of and priority to U.S. Provisional Patent Application No. 61/487,583, filed May 18, 2011, the contents of which are incorporated herein by reference.

BACKGROUND

The identification of new pharmacophores is of paramount biomedical importance and natural products have recently been regaining attention for this endeavor.[1] This renaissance is closely tied to the successful exploitation of the marine environment which harbors unmatched biodiversity that is presumably concomitant with chemical diversity.[2] In particular, marine cyanobacteria are prolific producers of bioactive secondary metabolites,[3] many of which are modified peptides or peptide-polyketide hybrids with promising antitumor activities, such as dolastatin 10,[4] curacin A,[5] and apratoxin A.[6] As a result of ongoing investigations to identify new drug leads from cyanobacteria, we report here the biological characterization of activity for class of a marine cyanobacterial metabolites and synthetic analogues with novel chemical scaffold and nanomolar antiproliferative activity. These findings provide new alternatives to address unmet needs in the treatment of proliferation diseases and disorders.

Modulation of cellular activity by apratoxins may be beneficial for cancer treatment and for immunosuppression, e.g., based on downregulation of receptors, inhibition of STAT3 activity and of T-cell activation. As such, other diseases that may be treated with apratoxin-based agents include other diseases where receptor downregulation may be beneficial, e.g., autoimmune diseases, some which may be associated with chemokine receptors (e.g., multiple sclerosis), or inflammation. These findings provide new alternatives to address unmet needs in the treatment of the aforementioned diseases, disorders, and symptoms thereof. Modulation of cellular activity by apratoxins may also be beneficial to disorders that are associated with enhanced secretory pathway activity.

BRIEF SUMMARY OF THE INVENTION

The invention is directed towards macrocyclic compounds, their mechanism of action, and methods of modulating proliferation activity, and methods of treating proliferation disease and disorders.

In one embodiment, the invention provides a compound according to formula (I):

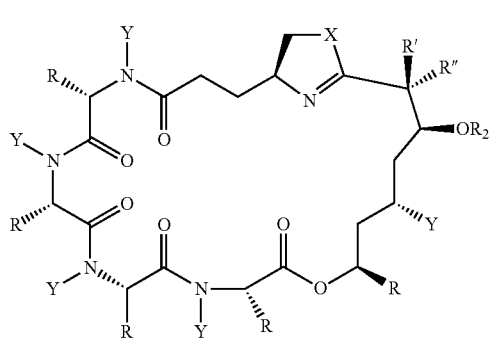

(I)

wherein:
Each X is independently S or O;
Each Y is independently H or Me;
Each R' is independently H, or alkyl;
Each R" is independently H, or alkyl;
Each R is independently alkyl optionally substituted with OH, OMe, SH, SMe, optionally substituted phenyl, $NH_2$, NH-alkyl, or N(alkyl)(alkyl); or each R is independently the side chain of a naturally-occurring or non-natural amino acid (including, e.g., phenylalanine, tyrosine, tryptophan, histidine, serine, methionine, and the like);
or each Y and R and the adjacent atoms attached to them (nitrogen and carbon, respectively,) can combine to form a heterocyclic ring;
Each $R_2$ is independently H, alkyl, or —C(O)alkyl;
and pharmaceutically acceptable salts, solvates, or hydrates thereof.

In one embodiment, the invention provides a compound according to any of the formula (I'):

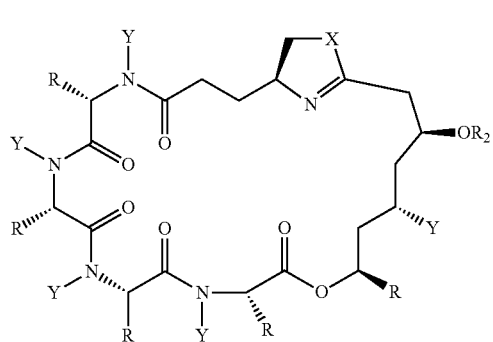

I' wherein:
Each X is independently S or O;
Each Y is independently H or Me;
Each R is independently alkyl optionally substituted with OH, OMe, SH, SMe, optionally substituted phenyl, $NH_2$, NH-alkyl, or N(alkyl)(alkyl); or each R is independently the side chain of a naturally-occurring or non-natural amino acid (including, e.g., phenylalanine, tyrosine, tryptophan, histidine, serine, methionine, and the like);
and wherein each Y and R and the adjacent atoms attached to them (nitrogen and carbon, respectively,) can combine to form a heterocyclic ring;
Each $R_2$ is independently H, alkyl, or —C(O)alkyl;
and pharmaceutically acceptable salts, solvates, or hydrates thereof.

Another aspect is a compound of formula I, having formula II:

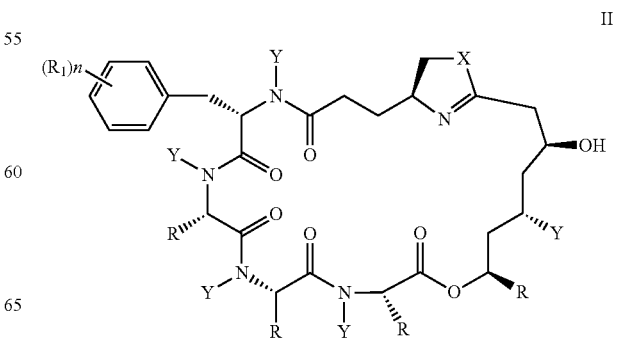

II wherein:
n is 0, 1, 2, 3, or 4;
each $R_1$ is independently OH, SH, thioalkoxy, alkoxy, halo, $NH_2$, NH-alkyl, or N(alkyl)(alkyl).
In other aspects, the compound is of any of the formulae III to VIII wherein the variables are as defined in formula (I'):
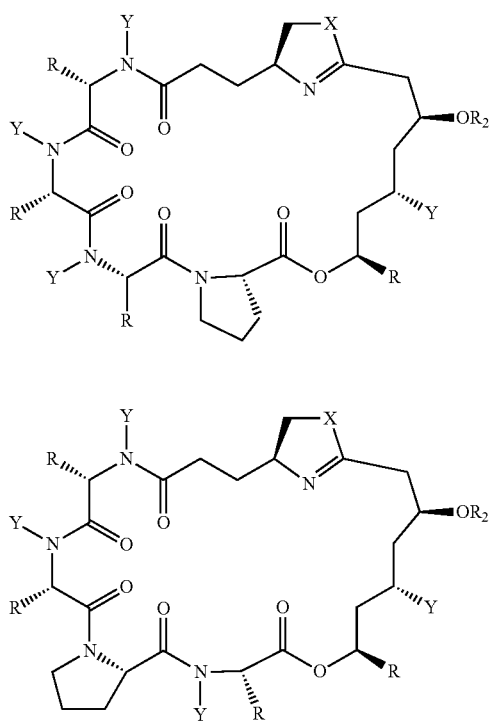
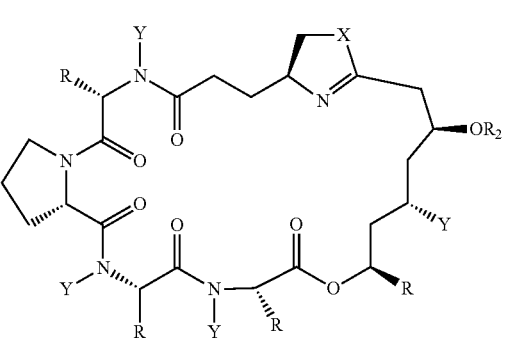
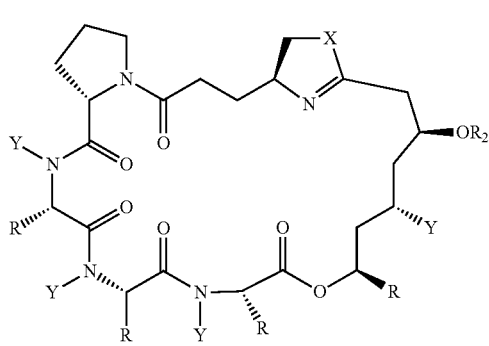
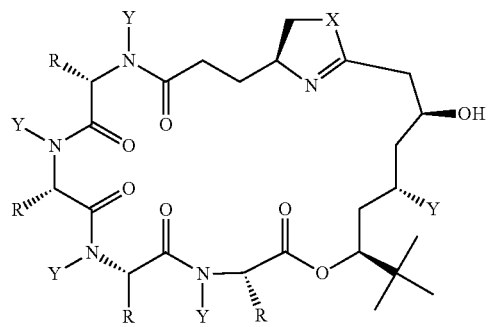
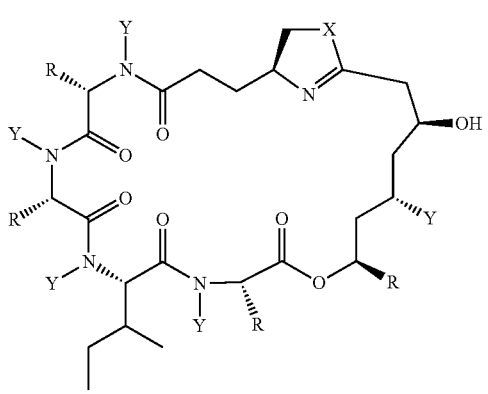
In other aspects, the compound is of any of the formulae IX to XIV wherein the variables are as defined in formula (I):
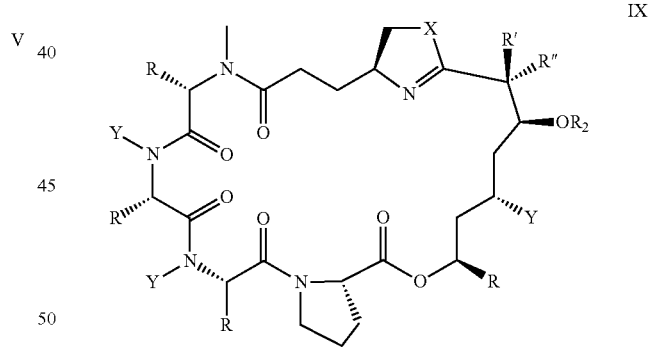
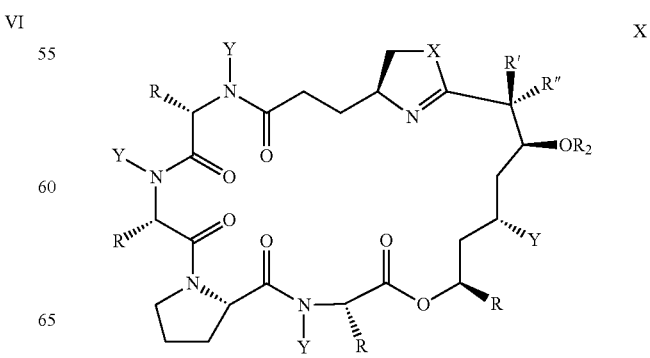

-continued

XI
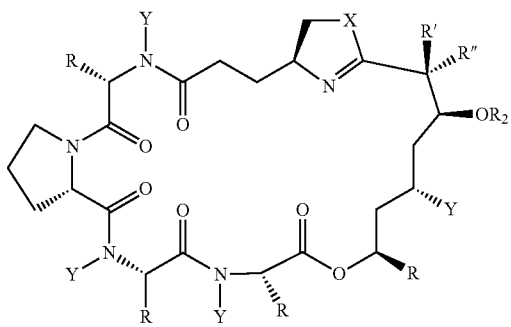

XII
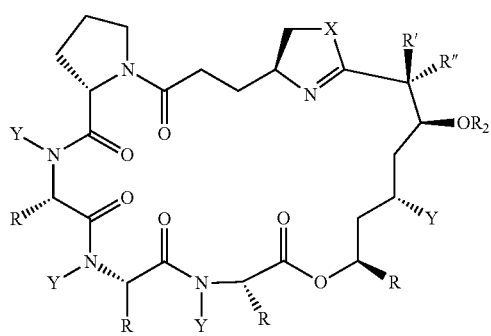

XIII
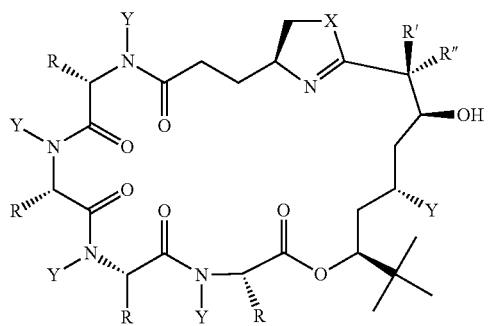

XIV
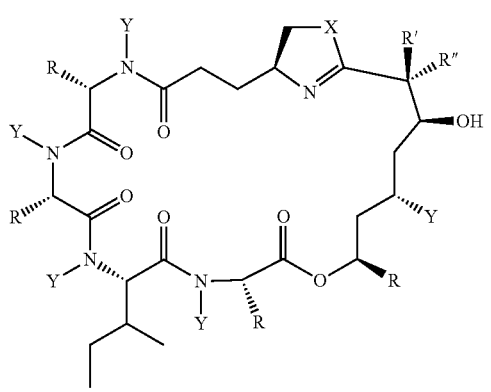

In another aspect, the compound is of formula XV:

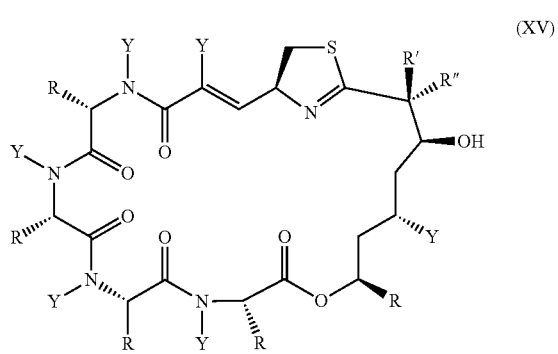

(XV)

wherein,
Each X is independently S or O;
Each Y is independently H or Me;
Each R' is independently H, or alkyl;
Each R" is independently H, or alkyl;
Each R is independently alkyl optionally substituted with OH, OMe, SH, SMe, optionally substituted phenyl, $NH_2$, NH-alkyl, or N(alkyl)(alkyl); or each R is independently the side chain of a naturally-occurring or non-natural amino acid (including, e.g., phenylalanine, tyrosine, tryptophan, histidine, serine, methionine, and the like);
or each Y and R and the adjacent atoms attached to them (nitrogen and carbon, respectively) can combine to form a heterocyclic ring;
Each $R_2$ is independently H, alkyl, or —C(O)alkyl;
and pharmaceutically acceptable salts, solvates, or hydrates thereof.

In another aspect, the compound is of formula XVI:

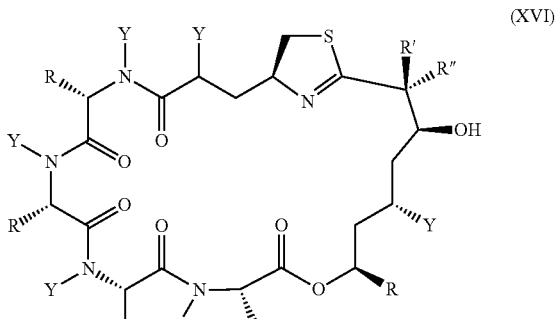

(XVI)

wherein,
Each X is independently S or O;
Each Y is independently H or Me;
Each R' is independently H, or alkyl;
Each R" is independently H, or alkyl;
Each R is independently alkyl optionally substituted with OH, OMe, SH, SMe, optionally substituted phenyl, $NH_2$, NH-alkyl, or N(alkyl)(alkyl); or each R is independently the side chain of a naturally-occurring or non-natural amino acid (including, e.g., phenylalanine, tyrosine, tryptophan, histidine, serine, methionine, and the like);
or each Y and R and the adjacent atoms attached to them (nitrogen and carbon, respectively,) can combine to form a heterocyclic ring;

Each $R_2$ is independently H, alkyl, or —C(O)alkyl;
and pharmaceutically acceptable salts, solvates, or hydrates thereof.
In other aspects, the compounds are those of the following formulae:
(14)
(15)
(16)
(17)
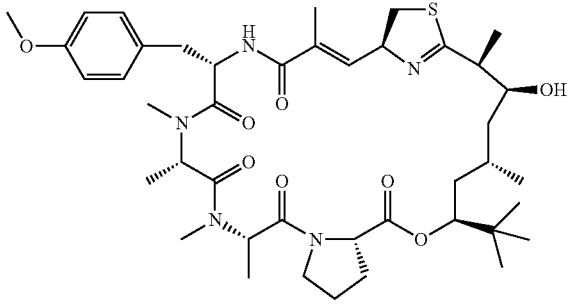
(18)
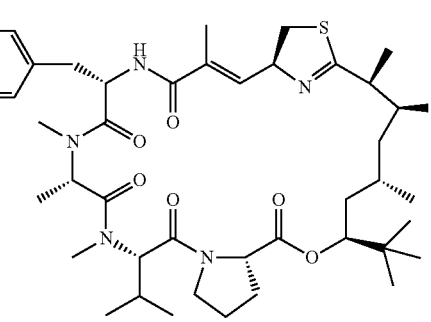
(19)
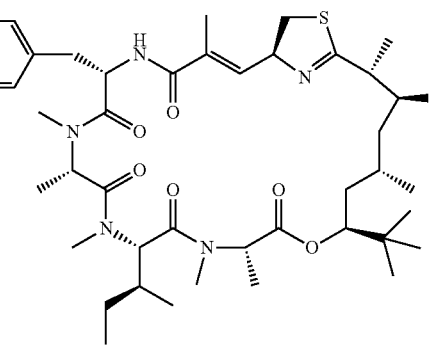
(20)
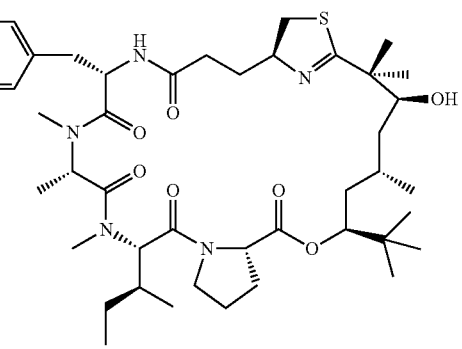
(21)

-continued

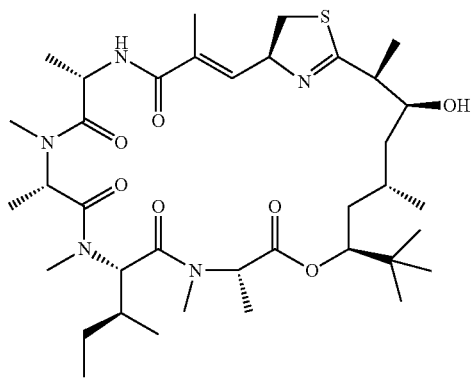

(22)

Another aspect is a compound herein, identified as an inhibitor of cotranslational translocation within the secretory pathway.

In another aspect, the invention provides a pharmaceutical composition comprising the compound of any of the formulae herein and a pharmaceutically acceptable carrier.

In one aspect, the invention provides a method of treating a disease, disorder, or symptom thereof in a subject, comprising administering to said subject a compound of any of the formulae herein (e.g., a compound of formula I; Apratoxins A-G).

In another aspect, the invention provides a method of treating a subject suffering from or susceptible to a STAT3 activity and/or T-cell activation related disorder or disease, wherein the subject has been identified as in need of treatment for a STAT3 activity and/or T-cell activation related disorder or disease, comprising administering to said subject in need thereof, an effective amount of a compound or pharmaceutical composition any of the formulae herein, such that said subject is treated for said disease or disorder. In aspects, the disease or disorder is one wherein receptor downregulation may be beneficial, e.g., autoimmune diseases, some which may be associated with chemokine receptors (e.g., multiple sclerosis), or inflammation.

In another aspect, the invention provides a method of treating a subject suffering from or susceptible to a disorder or disease wherein inhibition of cotranslational translocation within the secretory pathway leads to downregulation of receptors, other membrane proteins, or secreted proteins. In one aspect the method is that wherein a subject has been identified as in need of treatment for a disorder or disease wherein inhibition of cotranslational translocation within the secretory pathway leads to downregulation of receptors, other membrane proteins, or secreted proteins, comprising administering to said subject in need thereof, an effective amount of a compound or pharmaceutical composition of any of the formulae herein, such that said subject is treated for said disease or disorder. In other aspects, the method comprises treatment of a subject having a disease identified as one wherein downregulation of a receptor (or other membrane proteins, or secreted proteins) and/or inhibition of growth factor/cytokine secretion is caused by inhibition of cotranslational translocation. In aspects, the disease or disorder is one wherein receptor tyrosine kinase (RTK) receptor downregulation may be beneficial, e.g., cancer, autoimmune diseases, some which may be associated with chemokine receptors (e.g., multiple sclerosis), or inflammation. In one aspect, the downregulated target is any growth factor or cytokine (e.g., FGF1-4, VEGF, IL-6) or FGFR, PDGFR, IGFR, VEGFR and other receptors (e.g., FGFR1-4, or VEGFR2). In another aspect the disease or disorder is one modulated by any growth factor, FGF, VEGF or other receptor (e.g., FGF1-4, FGFR2 or VEGFR2) or cytokine whose secretion is inhibited by the described compounds.

In one aspect the methods herein are those wherein inhibition of growth factor/cytokine secretion is caused by the compounds of any of the formulae herein. In another aspect the methods herein are those wherein both downregulation of a receptor (e.g., any cited herein) and inhibition of growth factor/cytokine secretion is caused by the compounds of any of the formulae herein.

In one aspect the methods herein are those wherein the compounds of any of the formulae herein inhibit a receptor (e.g., any cited herein; growth factor, cytokine, an RTK, etc.). In one aspect the methods herein are those wherein the compounds of any of the formulae herein inhibit a ligand of a receptor (e.g., any cited herein; growth factor, cytokine, an RTK, etc.). In one aspect the methods herein are those wherein the compounds of any of the formulae herein inhibit a receptor (e.g., any cited herein; growth factor, cytokine, an RTK, etc.) and inhibit a ligand of a receptor (e.g., any cited herein; growth factor, cytokine, an RTK, etc.). In one aspect the methods herein are those wherein the compounds of any of the formulae herein inhibit a receptor (e.g., any cited herein; growth factor, cytokine, an RTK, etc.) and/or inhibit a ligand of that receptor (e.g., any cited herein; growth factor, cytokine, an RTK, etc.).

In another aspect, inhibition of cotranslational translocation using the compounds herein (e.g., formula I) results in the downregulation of certain ER proteins such as CANX, TXNDC5, PDI, CALR, BIP, or RPN1.

In another aspect, the disease or disorder is Hashimoto's thyroiditis, Pernicious anemia, Addison's disease, Type I diabetes, Rheumatoid arthritis, Systemic lupus erythematosus, Dermatomyositis, Sjogren syndrome, Lupus erythematosus, Multiple sclerosis, Myasthenia gravis, Reactive arthritis, Grave's disease, or Celiac disease—sprue. In another aspect, the disease or disorder is cystic fibrosis.

In other aspects, the invention provides a method of modulating the proliferation activity in a subject, comprising contacting the subject with a compound of any of the formulae herein, in an amount and under conditions sufficient to modulate proliferation activity.

In one aspect, the invention provides a method of treating a subject suffering from or susceptible to a proliferation related disorder or disease, comprising administering to the subject an effective amount of a compound or pharmaceutical composition any of the formulae herein.

In another aspect, the invention provides a method of treating a subject suffering from or susceptible to a proliferation related activity related disorder or disease, wherein the subject has been identified as in need of treatment for a proliferation related disorder or disease, comprising administering to said subject in need thereof, an effective amount of a compound or pharmaceutical composition of any of the formulae herein, such that said subject is treated for said disorder.

In another aspect, the invention provides a method of treating a subject suffering from or susceptible to a cell proliferation related disorder or disease, wherein the subject has been identified as in need of treatment for a cell proliferation related disorder or disease, comprising administering to said subject in need thereof, an effective amount of a compound or pharmaceutical composition of any of the formulae herein, such that cell proliferation in said subject is modulated (e.g., down regulated). In another aspect, the compounds delineated herein preferentially target cancer cells over nontransformed cells.

In another aspect, the invention provides a method of treating a subject suffering from or susceptible to a disorder or disease, wherein the subject has been identified as in need of treatment for a disorder or disease, comprising administering to said subject in need thereof, an effective amount of a compound or pharmaceutical composition thereof wherein the compound inhibits a target (e.g., any cited herein; growth factor, cytokine, an RTK, etc.) and/or inhibits a ligand of that target (e.g., any cited herein; growth factor, cytokine, an RTK, etc.). In one aspect, the compound is any of the formulae herein, or composition thereof.

Another aspect is a kit comprising an effective amount of an apratoxin compound identified as an inhibitor of cotranslational translocation of proteins destined for the secretory pathway (e.g., formula I compound), in unit dosage form, together with instructions for administering the compound to a subject suffering from or susceptible to a cell proliferation disorder.

Another aspect is a method of modulating the activity of cell proliferation in a subject, comprising identifying a subject in need of inhibition of cotranslational translocation of proteins destined for the secretory pathway with a compound identified as an inhibitor of cotranslational translocation of proteins destined for the secretory pathway, and administering to said subject in need thereof, an effective amount of a compound or pharmaceutical composition of any of the formulae herein (e.g., Formula I), in an amount and under conditions sufficient to modulate cell proliferation. In aspects, the inhibition of cotranslational translocation of proteins destined for the secretory pathway can be through modulation of other targets, or can additionally affect targets in the endoplasmic reticulum (e.g., ER proteins, including those delineated herein).

Another aspect is a method of treating a subject suffering from or susceptible to a cell proliferation related disorder or disease (e.g., cancer), wherein the subject has been identified as in need of treatment for a cell proliferation related disorder or disease by downregulation of a receptor tyrosine kinase, comprising administering to said subject in need thereof, an effective amount of an apratoxin compound, or apratoxin compound derivative, or pharmaceutical composition comprising a an apratoxin compound, or apratoxin compound derivative thereof, such that said subject is treated for said disorder.

Another aspect is a method of treating a subject suffering from or susceptible to a disorder or disease wherein growth factor and cytokine (ligand) downregulation is beneficial, particularly diseases including cancers that are driven by autocrine loops (e.g., colon cancer), wherein the subject has been identified as in need of treatment for a such disorder or disease, comprising administering to said subject in need thereof, an effective amount of an compound herein (or composition thereof), such that said subject is treated for said disorder.

In a specific aspect, the invention provides a method of treating cancer, tumor growth, cancer of the colon, breast, bone, brain and others (e.g., osteosarcoma, neuroblastoma, colon adenocarcinoma), chronic myelogenous leukemia (CML), acute myeloid leukemia (AML), acute promyelocytic leukemia (APL), comprising administering to said subject in need thereof, an effective amount of a compound delineated herein (e.g., any of the formulae herein), and pharmaceutically acceptable salts thereof. Other cancers that may be treated by the compositions and methods of the invention include cardiac cancer (e.g., sarcoma, myxoma, rhabdomyoma, fibroma, lipoma and teratoma); lung cancer (e.g., bronchogenic carcinoma, alveolar carcinoma, bronchial adenoma, sarcoma, lymphoma, chondromatous hamartoma, mesothelioma); various gastrointestinal cancer (e.g., cancers of esophagus, stomach, pancreas, small bowel, and large bowel); genitourinary tract cancer (e.g., kidney, bladder and urethra, prostate, testis; liver cancer (e.g., hepatoma, cholangiocarcinoma, hepatoblastoma, angiosarcoma, hepatocellular adenoma, hemangioma); bone cancer (e.g., osteogenic sarcoma, fibrosarcoma, malignant fibrous histiocytoma, chondrosarcoma, Ewing's sarcoma, malignant lymphoma, multiple myeloma, malignant giant cell tumor chordoma, osteochronfroma, benign chondroma, chondroblastoma, chondromyxofibroma, osteoid osteoma and giant cell tumors); cancers of the nervous system (e.g., of the skull, meninges, brain, and spinal cord); gynecological cancers (e.g., uterus, cervix, ovaries, vulva, vagina); hematologic cancer (e.g., cancers relating to blood, Hodgkin's disease, non-Hodgkin's lymphoma); skin cancer (e.g., malignant melanoma, basal cell carcinoma, squamous cell carcinoma, Karposi's sarcoma, moles dysplastic nevi, lipoma, angioma, dermatofibroma, keloids, psoriasis); and cancers of the adrenal glands (e.g., neuroblastoma). Other cancers that may be treated using the methods herein include, cervical, ovarian, bladder, pancreatic, and brain.

DETAILED DESCRIPTION

Definitions

In order that the invention may be more readily understood, certain terms are first defined here for convenience.

As used herein, the term "treating" a disorder encompasses preventing, ameliorating, mitigating and/or managing the disorder and/or conditions that may cause the disorder. The terms "treating" and "treatment" refer to a method of alleviating or abating a disease and/or its attendant symptoms. In accordance with the present invention "treating" includes preventing, blocking, inhibiting, attenuating, protecting against, modulating, reversing the effects of and reducing the occurrence of e.g., the harmful effects of a disorder.

As used herein, "inhibiting" encompasses preventing, reducing and halting progression.

The term "modulate" refers to increases or decreases in the activity of a cell in response to exposure to a compound of the invention.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. Particularly, in embodiments the compound is at least 85% pure, more preferably at least 90% pure, more preferably at least 95% pure, and most preferably at least 99% pure.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

A "peptide" is a sequence of at least two amino acids. Peptides can consist of short as well as long amino acid sequences, including proteins.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid Amino acid mimetics refers to chemical compounds that have a structure that is different from the general chemical structure of an amino acid, but that functions in a manner similar to a naturally occurring amino acid.

The term "protein" refers to series of amino acid residues connected one to the other by peptide bonds between the alpha-amino and carboxy groups of adjacent residues.

Amino acids may be referred to herein by either their commonly known three letter symbols or by the one-letter symbols recommended by the IUPAC-IUB Biochemical Nomenclature Commission.

As to amino acid sequences, one of skill will recognize that individual substitutions, deletions or additions to a peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

Macromolecular structures such as polypeptide structures can be described in terms of various levels of organization. For a general discussion of this organization, see, e.g., Alberts et al., Molecular Biology of the Cell (3rd ed., 1994) and Cantor and Schimmel, Biophysical Chemistry Part I. The Conformation of Biological Macromolecules (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 50 to 350 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

The term "administration" or "administering" includes routes of introducing the compound(s) to a subject to perform their intended function. Examples of routes of administration which can be used include injection (subcutaneous, intravenous, parenterally, intraperitoneally, intrathecal), topical, oral, inhalation, rectal and transdermal.

The term "effective amount" includes an amount effective, at dosages and for periods of time necessary, to achieve the desired result. An effective amount of compound may vary according to factors such as the disease state, age, and weight of the subject, and the ability of the compound to elicit a desired response in the subject. Dosage regimens may be adjusted to provide the optimum therapeutic response. An effective amount is also one in which any toxic or detrimental effects (e.g., side effects) of the elastase inhibitor compound are outweighed by the therapeutically beneficial effects.

The phrases "systemic administration," "administered systemically", "peripheral administration" and "administered peripherally" as used herein mean the administration of a compound(s), drug or other material, such that it enters the patient's system and, thus, is subject to metabolism and other like processes.

The term "therapeutically effective amount" refers to that amount of the compound being administered sufficient to prevent development of or alleviate to some extent one or more of the symptoms of the condition or disorder being treated.

A therapeutically effective amount of compound (i.e., an effective dosage) may range from about 0.005 µg/kg to about 200 mg/kg, preferably about 0.1 mg/kg to about 200 mg/kg, more preferably about 10 mg/kg to about 100 mg/kg of body weight. In other embodiments, the therapeutically effect amount may range from about 1.0 pM to about 500 nM. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a compound can include a single treatment or, preferably, can include a series of treatments. In one example, a subject is treated with a compound in the range of between about 0.005 µg/kg to about 200 mg/kg of body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of a compound used for treatment may increase or decrease over the course of a particular treatment.

The term "chiral" refers to molecules which have the property of non-superimposability of the mirror image partner, while the term "achiral" refers to molecules which are superimposable on their mirror image partner.

The term "diastereomers" refers to stereoisomers with two or more centers of dissymmetry and whose molecules are not mirror images of one another.

The term "enantiomers" refers to two stereoisomers of a compound which are non-superimposable mirror images of one another. An equimolar mixture of two enantiomers is called a "racemic mixture" or a "racemate."

The term "isomers" or "stereoisomers" refers to compounds which have identical chemical constitution, but differ with regard to the arrangement of the atoms or groups in space.

The term "prodrug" includes compounds with moieties which can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters. Prodrugs which are converted to active forms through other mechanisms in vivo are also included.

The term "subject" refers to animals such as mammals, including, but not limited to, primates (e.g., humans), cows, sheep, goats, horses, dogs, cats, rabbits, rats, mice and the like. In certain embodiments, the subject is a human.

Furthermore the compounds of the invention include olefins having either geometry: "Z" refers to what is referred to as a "cis" (same side) conformation whereas "E" refers to what is referred to as a "trans" (opposite side) conformation. With respect to the nomenclature of a chiral center, the terms "d" and "l" configuration are as defined by the IUPAC Recommendations. As to the use of the terms, diastereomer, racemate, epimer and enantiomer, these will be used in their normal context to describe the stereochemistry of preparations.

As used herein, the term "alkyl" refers to a straight-chained or branched hydrocarbon group containing 1 to 12 carbon atoms. The term "lower alkyl" refers to a C1-C6 alkyl chain. Examples of alkyl groups include methyl, ethyl, n-propyl, isopropyl, tert-butyl, and n-pentyl. Alkyl groups may be optionally substituted with one or more substituents.

The term "alkenyl" refers to an unsaturated hydrocarbon chain that may be a straight chain or branched chain, containing 2 to 12 carbon atoms and at least one carbon-carbon double bond. Alkenyl groups may be optionally substituted with one or more substituents.

The term "alkynyl" refers to an unsaturated hydrocarbon chain that may be a straight chain or branched chain, containing the 2 to 12 carbon atoms and at least one carbon-carbon triple bond. Alkynyl groups may be optionally substituted with one or more substituents.

The $sp^2$ or sp carbons of an alkenyl group and an alkynyl group, respectively, may optionally be the point of attachment of the alkenyl or alkynyl groups.

The term "alkoxy" refers to an —O-alkyl radical.

As used herein, the term "halogen", "hal" or "halo" means —F, —Cl, —Br or —I.

The term "cycloalkyl" refers to a hydrocarbon 3-8 membered monocyclic or 7-14 membered bicyclic ring system having at least one saturated ring or having at least one non-aromatic ring, wherein the non-aromatic ring may have some degree of unsaturation. Cycloalkyl groups may be optionally substituted with one or more substituents. In one embodiment, 0, 1, 2, 3, or 4 atoms of each ring of a cycloalkyl group may be substituted by a substituent. Representative examples of cycloalkyl group include cyclopropyl, cyclopentyl, cyclohexyl, cyclobutyl, cycloheptyl, cyclopentenyl, cyclopentadienyl, cyclohexenyl, cyclohexadienyl, and the like.

The term "aryl" refers to a hydrocarbon monocyclic, bicyclic or tricyclic aromatic ring system. Aryl groups may be optionally substituted with one or more substituents. In one embodiment, 0, 1, 2, 3, 4, 5 or 6 atoms of each ring of an aryl group may be substituted by a substituent. Examples of aryl groups include phenyl, naphthyl, anthracenyl, fluorenyl, indenyl, azulenyl, and the like.

The term "heteroaryl" refers to an aromatic 5-8 membered monocyclic, 8-12 membered bicyclic, or 11-14 membered tricyclic ring system having 1-4 ring heteroatoms if monocyclic, 1-6 ring heteroatoms if bicyclic, or 1-9 heteroatoms if tricyclic, said heteroatoms selected from O, N, or S, and the remainder ring atoms being carbon (with appropriate hydrogen atoms unless otherwise indicated). Heteroaryl groups may be optionally substituted with one or more substituents. In one embodiment, 0, 1, 2, 3, or 4 atoms of each ring of a heteroaryl group may be substituted by a substituent. Examples of heteroaryl groups include pyridyl, furanyl, thienyl, pyrrolyl, oxazolyl, oxadiazolyl, imidazolyl thiazolyl, isoxazolyl, quinolinyl, pyrazolyl, isothiazolyl, pyridazinyl, pyrimidinyl, pyrazinyl, triazinyl, isoquinolinyl, indazolyl, and the like.

The term "heterocycloalkyl" refers to a nonaromatic 3-8 membered monocyclic, 7-12 membered bicyclic, or 10-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si, wherein the nonaromatic ring system is completely saturated. Heterocycloalkyl groups may be optionally substituted with one or more substituents. In one embodiment, 0, 1, 2, 3, or 4 atoms of each ring of a heterocycloalkyl group may be substituted by a substituent. Representative heterocycloalkyl groups include piperidinyl, piperazinyl, tetrahydropyranyl, morpholinyl, thiomorpholinyl, 1,3-dioxolane, tetrahydrofuranyl, tetrahydrothienyl, thiirenyl, and the like.

The term "alkylamino" refers to an amino substituent which is further substituted with one or two alkyl groups. The term "aminoalkyl" refers to an alkyl substituent which is further substituted with one or more amino groups. The term "hydroxyalkyl" or "hydroxylalkyl" refers to an alkyl substituent which is further substituted with one or more hydroxyl groups. The alkyl or aryl portion of alkylamino, aminoalkyl, mercaptoalkyl, hydroxyalkyl, mercaptoalkoxy, sulfonylalkyl, sulfonylaryl, alkylcarbonyl, and alkylcarbonylalkyl may be optionally substituted with one or more substituents.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

Alkylating agents are any reagent that is capable of effecting the alkylation of the functional group at issue (e.g., oxygen atom of an alcohol, nitrogen atom of an amino group). Alkylating agents are known in the art, including in the references cited herein, and include alkyl halides (e.g., methyl iodide, benzyl bromide or chloride), alkyl sulfates (e.g., methyl sulfate), or other alkyl group-leaving group combinations known in the art. Leaving groups are any stable species that can detach from a molecule during a reaction (e.g., elimination reaction, substitution reaction) and are known in the art, including in the references cited herein, and include halides (e.g., I—, Cl—, Br—, F—), hydroxy, alkoxy (e.g., —OMe, —O-t-Bu), acyloxy anions (e.g., —OAc, —OC(O) $CF_3$), sulfonates (e.g., mesyl, tosyl), acetamides (e.g., —NHC(O)Me), carbamates (e.g., N(Me)C(O)Ot-Bu), phosphonates (e.g., —OP(O)(OEt)$_2$), water or alcohols (protic conditions), and the like.

In certain embodiments, substituents on any group (such as, for example, alkyl, alkenyl, alkynyl, aryl, aralkyl, heteroaryl, heteroaralkyl, cycloalkyl, heterocycloalkyl) can be at any atom of that group, wherein any group that can be substituted (such as, for example, alkyl, alkenyl, alkynyl, aryl, aralkyl, heteroaryl, heteroaralkyl, cycloalkyl, heterocycloalkyl) can be optionally substituted with one or more substituents (which may be the same or different), each replacing a hydrogen atom. Examples of suitable substituents include, but are not limited to alkyl, alkenyl, alkynyl, cycloalkyl, heterocycloalkyl, aralkyl, heteroaralkyl, aryl, heteroaryl, halogen, haloalkyl, cyano, nitro, alkoxy, aryloxy, hydroxyl, hydroxylalkyl, oxo (i.e., carbonyl), carboxyl, formyl, alkylcarbonyl, alkylcarbonylalkyl, alkoxycarbonyl, alkylcarbonyloxy, aryloxycarbonyl, heteroaryloxy, heteroaryloxycarbonyl, thio, mercapto, mercaptoalkyl, arylsulfonyl, amino, aminoalkyl, dialkylamino, alkylcarbonylamino, alkylaminocarbonyl, alkoxycarbonylamino, alkylamino, arylamino, diarylamino, alkylcarbonyl, or arylamino-substituted aryl; arylalkylamino, aralkylaminocarbonyl, amido, alkylaminosulfonyl, arylaminosulfonyl, dialkylaminosulfonyl, alkylsulfonylamino, arylsulfonylamino, imino, carbamido, carbamyl, thioureido, thiocyanato, sulfoamido, sulfonylalkyl, sulfonylaryl, or mercaptoalkoxy.

Compounds of the Invention

Compounds delineated herein (i.e., Formula I) include salt, hydrate and solvates thereof. They include all compounds delineated in schemes herein, whether intermediate or final compounds in a process.

Compounds of the invention can be obtained from natural sources or made or modified made by means known in the art of organic synthesis. Methods for optimizing reaction conditions, if necessary minimizing competing by-products, are known in the art. Reaction optimization and scale-up may advantageously utilize high-speed parallel synthesis equipment and computer-controlled microreactors (e.g. *Design And Optimization in Organic Synthesis, 2nd Edition*, Carlson R, Ed, 2005; Elsevier Science Ltd; Jähnisch, K et al, Angew. Chem. Int. Ed. Engl. 2004 43: 406; and references therein). Additional reaction schemes and protocols may be determined by the skilled artesian by use of commercially available structure-searchable database software, for instance, SciFinder® (CAS division of the American Chemical Society) and CrossFire Beilstein® (Elsevier MDL), or by appropriate keyword searching using an internet search engine such as Google® or keyword databases such as the US Patent and Trademark Office text database. For example, compounds of formulae herein can be made using methodology known in the art, including Doi et al., Org Lett. 2006 Feb. 2; 8(3):531-4; Ma, et al., Chemistry. 2006 Oct. 10; 12(29):7615-26; and Chen et al., Proc Natl Acad Sci USA. 2004 Aug. 17; 101(33): 12067-72.

The compounds herein may also contain linkages (e.g., carbon-carbon bonds) wherein bond rotation is restricted about that particular linkage, e.g. restriction resulting from the presence of a ring or double bond. Accordingly, all cis/trans and E/Z isomers are expressly included in the present invention. The compounds herein may also be represented in multiple tautomeric forms, in such instances, the invention expressly includes all tautomeric forms of the compounds described herein, even though only a single tautomeric form may be represented. All such isomeric forms of such compounds herein are expressly included in the present invention. All crystal forms and polymorphs of the compounds described herein are expressly included in the present invention. All hydrate and solvate forms of the compounds described herein are expressly included in the present invention. Also embodied are extracts and fractions comprising compounds of the invention. The term isomers is intended to include diastereoisomers, enantiomers, regioisomers, structural isomers, rotational isomers, tautomers, and the like. For compounds which contain one or more stereogenic centers, e.g., chiral compounds, the methods of the invention may be carried out with an enantiomerically enriched compound, a racemate, or a mixture of diastereomers.

Preferred enantiomerically enriched compounds have an enantiomeric excess of 50% or more, more preferably the compound has an enantiomeric excess of 60%, 70%, 80%, 90%, 95%, 98%, or 99% or more. In preferred embodiments, only one enantiomer or diastereomer of a chiral compound of the invention is administered to cells or a subject.

The compounds of the formulae herein can be synthesized using methodology similarly to that shown in Scheme I below:

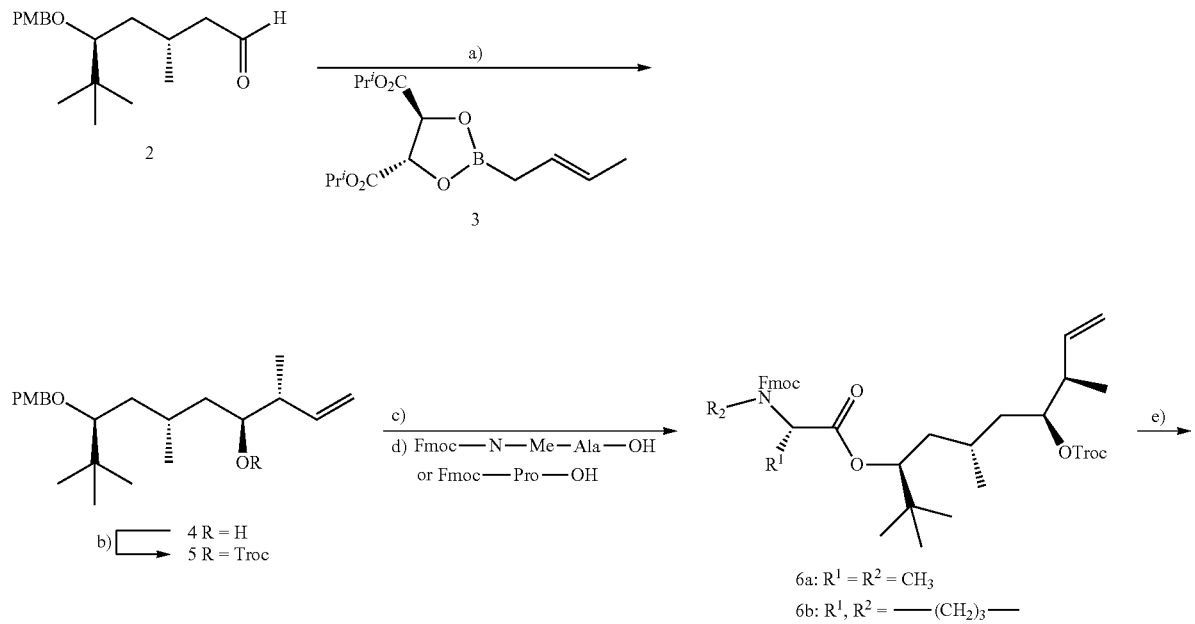

-continued

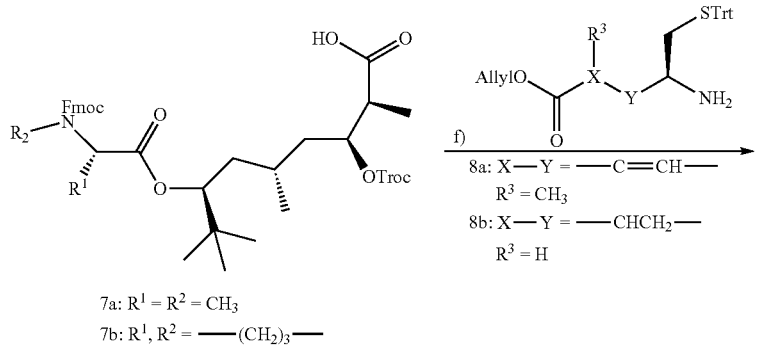

7a: $R^1 = R^2 = CH_3$
7b: $R^1, R^2 = —(CH_2)_3—$

8a: $X—Y = —C\equiv CH—$
   $R^3 = CH_3$
8b: $X—Y = —CHCH_2—$
   $R^3 = H$

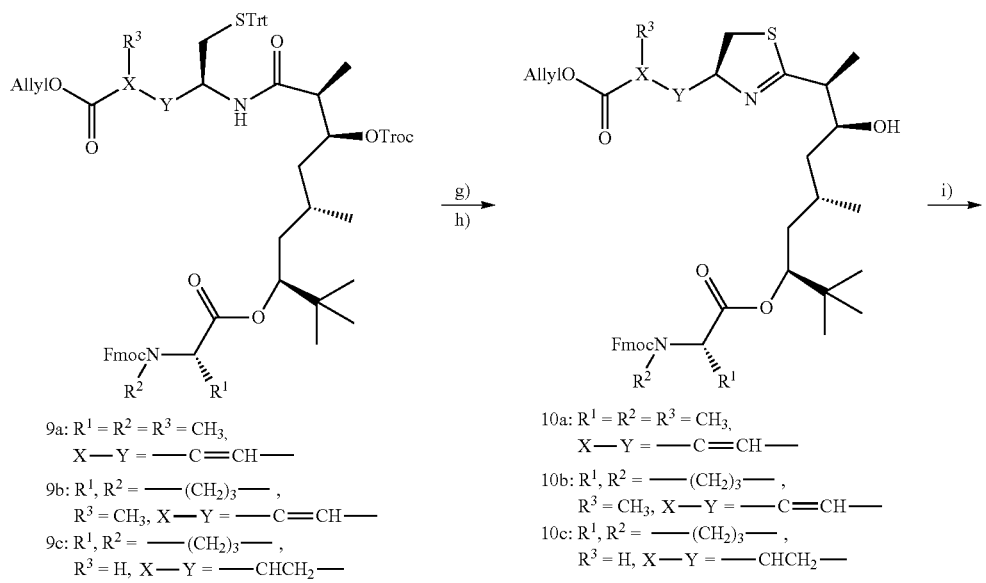

9a: $R^1 = R^2 = R^3 = CH_3$,
   $X—Y = —C\equiv CH—$
9b: $R^1, R^2 = —(CH_2)_3—$,
   $R^3 = CH_3$, $X—Y = —C\equiv CH—$
9c: $R^1, R^2 = —(CH_2)_3—$,
   $R^3 = H$, $X—Y = —CHCH_2—$ 10a: $R^1 = R^2 = R^3 = CH_3$,
   $X—Y = —C\equiv CH—$
10b: $R^1, R^2 = —(CH_2)_3—$,
   $R^3 = CH_3$, $X—Y = —C\equiv CH—$
10c: $R^1, R^2 = —(CH_2)_3—$,
   $R^3 = H$, $X—Y = —CHCH_2—$

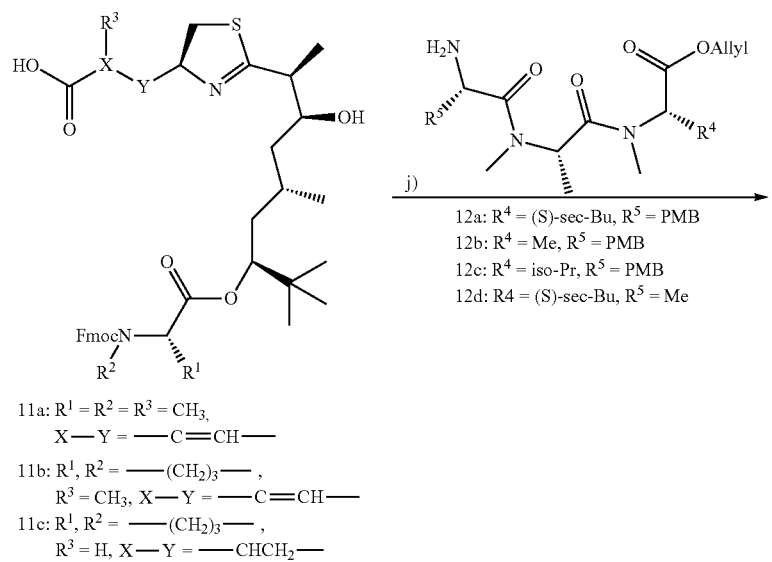

11a: $R^1 = R^2 = R^3 = CH_3$,
   $X—Y = —C\equiv CH—$
11b: $R^1, R^2 = —(CH_2)_3—$,
   $R^3 = CH_3$, $X—Y = —C\equiv CH—$
11c: $R^1, R^2 = —(CH_2)_3—$,
   $R^3 = H$, $X—Y = —CHCH_2—$ 12a: $R^4 = (S)$-sec-Bu, $R^5 = PMB$
12b: $R^4 = Me$, $R^5 = PMB$
12c: $R^4 = $ iso-Pr, $R^5 = PMB$
12d: $R4 = (S)$-sec-Bu, $R^5 = Me$ -continued

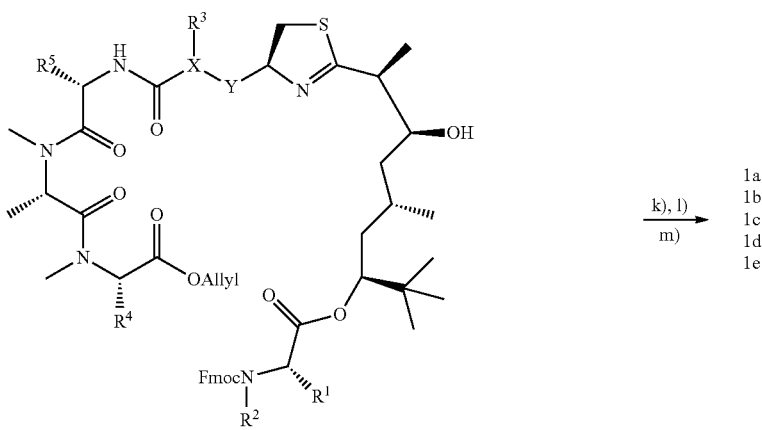

13a: $R^1 = R^2 = R^3 = CH_3$, $R^4 = (S)\text{-sec-Bu}$, $R^5 = PMB$, $X-Y = -C\equiv CH-$
13b: $R^1, R^2 = -(CH_2)_3-$, $R^3 = R^4 = CH_3$, $R^5 = PMB$, $X-Y = -C\equiv CH-$
13c: $R^1, R^2 = -(CH_2)_3-$, $R^3 = CH_3$, $R^4 = \text{iso-Pr}$, $R^5 = PMB$, $X-Y = -C\equiv CH-$
13d: $R^1, R^2 = -(CH_2)_3-$, $R^3 = R^5 = CH_3$, $R^4 = (S)\text{-sec-Bu}$, $X-Y = -C\equiv CH-$
13e: $R^1, R^2 = -(CH_2)_3-$, $R^3 = H$, $R^4 = (S)\text{-sec-Bu}$, $R^5 = PMB$, $X-Y = -CHCH_2-$ Preparation of the analogues of apratoxin A. a) MS 4A, Toluene, -78° C.; b) TrocCl, DMAP, Pyridine, CH$_2$Cl$_2$; c) DDQ, CH$_2$Cl$_2$—H$_2$O; d) Cl$_3$C$_6$H$_2$COCl, DIEA, THF, DMAP, toluene; e) OsO$_4$, Oxone, NaIO$_4$; f) HATU, DIEA, CH$_2$Cl$_2$; g) Ph$_3$P(O), Tf$_2$O, CH$_2$Cl$_2$, 0° C.; h) Zn, NH$_4$OAc, THF; i) Pd(Ph$_3$)$_4$, N-methylaniline, THF; j) HATU, DIEA, CH$_2$Cl$_2$; k) Pd(Ph$_3$)$_4$, N-methylaniline, THF; l) Et$_2$NH, MeCN; m) HATU, DIEA, CH$_2$Cl$_2$. Troc = 2,2,2-trichloroethoxycarbonyl, DMAP = 4-(dimethylamino)pyridine, DDQ = 2,3-dichloro-4,5-dicyanobenzoquinone; Fmoc = 9-fluorenylmethoxycarbonyl, Trt = triphenylmethyl, HATU = O-(7-Azabenzotriazol-1-yl)-N,N,N',N'-tetramethyluronium hexafluorophosphate, DIEA = diisopropylethylamine, Tf = trifluoro.

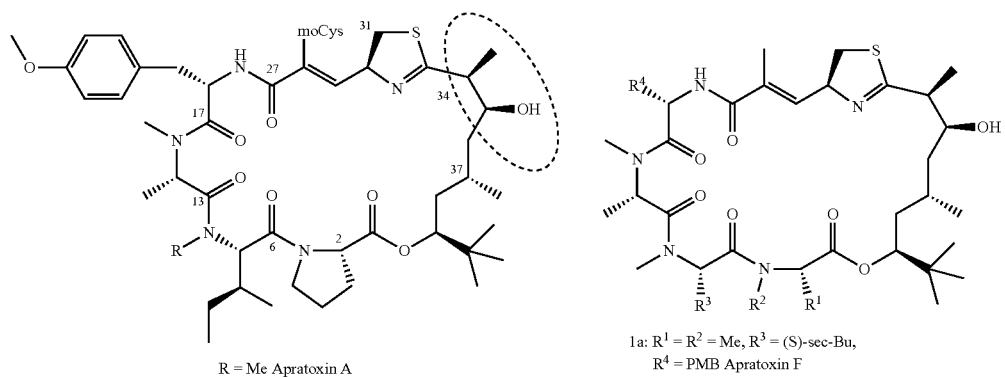

R = Me Apratoxin A
R = H Apratoxin B

1a: $R^1 = R^2 = Me$, $R^3 = (S)\text{-sec-Bu}$, $R^4 = PMB$ Apratoxin F
1b: $R^1, R^2 = -CH_2CH_2CH_2-$, $R^3 = Me$, $R^4 = PMB$ Apratoxin S1
1c: $R^1, R^2 = -CH_2CH_2CH_2-$, $R^3 = \text{iso-Pr}$, $R^4 = PMB$ Apratoxin S2
1d: $R^1, R^2 = -CH_2CH_2CH_2-$, $R^3 = (S)\text{-sec-Bu}$, $R^4 = Me$ Apratoxin S3

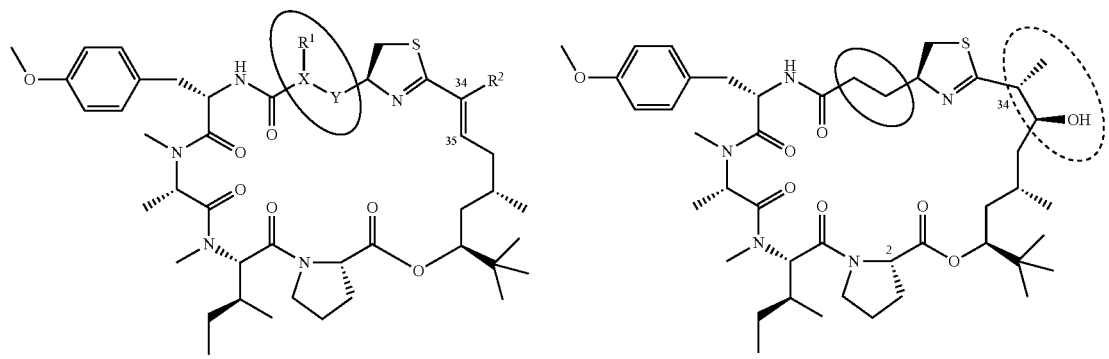

$R^1 = R^2 = Me$, $X-Y = -C\equiv CH-$
E-dehydroapratoxin A
$R^1 = R^2 = H$, $X-Y = -CH_2CH_2-$
Apratoxin E 1e: Apratoxin S4

Furthermore, for example, compound 14 herein can be synthesized using the method delineated in Scheme I by using the allyl analogue (i.e., (4S,5S)-diisopropyl 2-allyl-1,3,2-dioxaborolane-4,5-dicarboxylate) of Roush's (E-) crotylboronate reagent in place of the but-2-enyl crotylboronate (3).

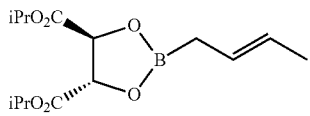

(4S,5S)-diisopropyl 2-((E)-but-2-enyl)-1,3,2-dioxaborolane-4,5-dicarboxylate

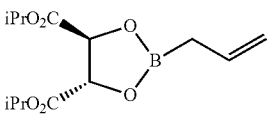

(4S,5S)-diisopropyl 2-allyl-1,3,2-dioxaborolane-4,5-dicarboxylate

Des-methyl compounds of the invention can also be made using C34-desmethyl segments (i.e., compounds C) made essentially as illustrated in the representative methods below:

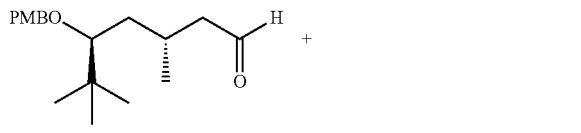

A

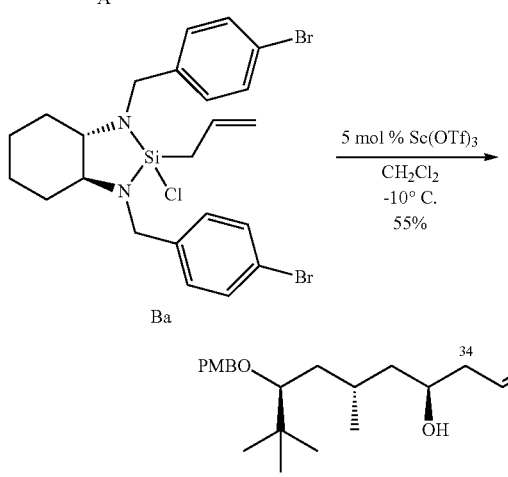

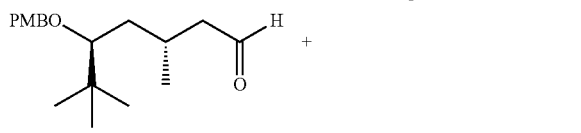

A

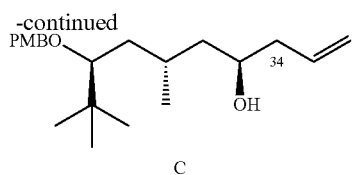

C

Methods of Treatment

In one aspect, the invention provides a method of treating a disease, disorder, or symptom thereof in a subject, comprising contacting the subject with a compound any of the formulae herein, in an amount and under conditions sufficient to treat the disease, disorder, or symptom thereof in the subject.

In one aspect, the invention provides a method of treating a disease, disorder, or symptom thereof in a subject, wherein the disorder is Hashimoto's thyroiditis, Pernicious anemia, Addison's disease, Type I diabetes, Rheumatoid arthritis, Systemic lupus erythematosus, Dermatomyositis, Sjogren syndrome, Lupus erythematosus, Multiple sclerosis, Myasthenia gravis, Reactive arthritis, Grave's disease, Celiac disease—sprue or cystic fibrosis.

In one aspect, the invention provides a method of modulating the proliferation activity of a cell in a subject, comprising contacting the subject with a compound of any of the formulae herein, in an amount and under conditions sufficient to modulate cell proliferation activity.

In one embodiment, the modulation is inhibition.

In another aspect, the invention provides a method of treating a subject suffering from or susceptible to a cell proliferation related disorder or disease, comprising administering to the subject an effective amount of a compound or pharmaceutical composition of any of the formulae herein.

In other aspects, the invention provides a method of treating a subject suffering from or susceptible to a cell proliferation related disorder or disease, wherein the subject has been identified as in need of treatment for a cell proliferation related disorder or disease, comprising administering to said subject in need thereof, an effective amount of a compound or pharmaceutical composition of any of the formulae herein, such that said subject is treated for said disorder.

In certain embodiments, the invention provides a method of treating a disorder, wherein the disorder is cancer (e.g., breast, colon, pancreas) or solid tumor.

In certain embodiments, the subject is a mammal, preferably a primate or human.

Methods delineated herein include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method).

In another embodiment, the invention provides a method as described above, wherein the effective amount of the compound of any of the formulae herein ranges from about 0.005 µg/kg to about 200 mg/kg. In certain embodiments, the effective amount of the compound of any of the formulae herein ranges from about 0.1 mg/kg to about 200 mg/kg. In a further embodiment, the effective amount of compound of any of the formulae herein ranges from about 10 mg/kg to 100 mg/kg.

In other embodiments, the invention provides a method as described above wherein the effective amount of the compound of any of the formulae herein ranges from about 1.0 pM to about 500 nM. In certain embodiments, the effective amount ranges from about 10.0 pM to about 1000 pM. In another embodiment, the effective amount ranges from about 1.0 nM to about 10 nM.

In another embodiment, the invention provides a method as described above, wherein the compound of any of the formulae herein is administered intravenously, intramuscularly, subcutaneously, intracerebroventricularly, orally or topically.

In other embodiments, the invention provides a method as described above, wherein the compound of any of the formulae herein is administered alone or in combination with one or more other therapeutics. In a further embodiment, the additional therapeutic agent is an anti-cancer agent, chemotherapeutic agent, an anti-angiogenesis agent, cytotoxic agent, or an anti-proliferation agent. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine (CA), 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, vincristine, vinblastine, etoposide, trimetrexate, teniposide, cisplatin and diethylstilbestrol (DES). See, generally, The Merck Manual of Diagnosis and Therapy, 15th Ed., pp. 1206-1228, Berkow et al., eds., Rahay, N.J., 1987).

Another object of the present invention is the use of a compound as described herein (e.g., of any formulae herein) in the manufacture of a medicament for use in the treatment of a cell proliferation disorder or disease. Another object of the present invention is the use of a compound as described herein (e.g., of any formulae herein) for use in the treatment of a cell proliferation disorder or disease.

Pharmaceutical Compositions

In one aspect, the invention provides a pharmaceutical composition comprising the compound of any of the formulae herein and a pharmaceutically acceptable carrier.

In another embodiment, the invention provides a pharmaceutical composition wherein the compound of any of the formulae herein is a compound of any of Formula I and a pharmaceutically acceptable carrier.

In another embodiment, the invention provides a pharmaceutical composition further comprising an additional therapeutic agent. In a further embodiment, the additional therapeutic agent is an anti-cancer agent, chemotherapeutic agent, an anti-angiogenesis agent, cytotoxic agent, or an anti-proliferation agent.

In one aspect, the invention provides a kit comprising an effective amount of a compound of any of the formulae herein, in unit dosage form, together with instructions for administering the compound to a subject suffering from or susceptible to a cell proliferation disease or disorder, including cancer, solid tumor, angiogenesis, etc.

The term "pharmaceutically acceptable salts" or "pharmaceutically acceptable carrier" is meant to include salts of the active compounds which are prepared with relatively non-toxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., Journal of Pharmaceutical Science 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

The invention also provides a pharmaceutical composition, comprising an effective amount a compound described herein and a pharmaceutically acceptable carrier. In an embodiment, compound is administered to the subject using a pharmaceutically-acceptable formulation, e.g., a pharmaceutically-acceptable formulation that provides sustained delivery of the compound to a subject for at least 12 hours, 24 hours, 36 hours, 48 hours, one week, two weeks, three weeks, or four weeks after the pharmaceutically-acceptable formulation is administered to the subject.

Actual dosage levels and time course of administration of the active ingredients in the pharmaceutical compositions of this invention may be varied so as to obtain an amount of the active ingredient which is effective to achieve the desired therapeutic response for a particular patient, composition, and mode of administration, without being toxic (or unacceptably toxic) to the patient.

In use, at least one compound according to the present invention is administered in a pharmaceutically effective amount to a subject in need thereof in a pharmaceutical carrier by intravenous, intramuscular, subcutaneous, or intracerebro ventricular injection or by oral administration or topical application. In accordance with the present invention, a compound of the invention may be administered alone or in conjunction with a second, different therapeutic. By "in conjunction with" is meant together, substantially simultaneously or sequentially. In one embodiment, a compound of the invention is administered acutely. The compound of the invention may therefore be administered for a short course of treatment, such as for about 1 day to about 1 week. In another embodiment, the compound of the invention may be administered over a longer period of time to ameliorate chronic disorders, such as, for example, for about one week to several months depending upon the condition to be treated.

By "pharmaceutically effective amount" as used herein is meant an amount of a compound of the invention, high enough to significantly positively modify the condition to be treated but low enough to avoid serious side effects (at a reasonable benefit/risk ratio), within the scope of sound medical judgment. A pharmaceutically effective amount of a compound of the invention will vary with the particular goal to be achieved, the age and physical condition of the patient being treated, the severity of the underlying disease, the duration of treatment, the nature of concurrent therapy and the specific apratoxin compound employed. For example, a therapeutically effective amount of a compound of the invention administered to a child or a neonate will be reduced proportionately in accordance with sound medical judgment. The effective amount of a compound of the invention will thus be the minimum amount which will provide the desired effect.

The compound may be administered parenterally or intraperitoneally. Dispersions can also be prepared, for example, in glycerol, liquid polyethylene glycols, and mixtures thereof, and in oils.

The pharmaceutical forms suitable for injectable use include sterile aqueous solutions (where water soluble) or dispersions and sterile powders for the extemporaneous preparation of sterile injectable solutions or dispersions. In all cases the form must be sterile and must be fluid to the extent that easy syringability exists. It must be stable under the conditions of manufacture and storage. The carrier can be a solvent or dispersion medium containing, for example, water, DMSO, ethanol, polyol (for example, glycerol, propylene glycol, liquid polyethylene glycol, and the like), suitable mixtures thereof and vegetable oils. The proper fluidity can be maintained, for example, by the use of a coating such as lecithin, by the maintenance of the required particle size in the case of dispersion. In many cases it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the compound of the invention in the required amount in the appropriate solvent with various of the other ingredients enumerated above, as required, followed by filtered sterilization. Generally, dispersions are prepared by incorporating the various sterilized compounds into a sterile vehicle which contains the basic dispersion medium and the required other ingredients from those enumerated above. In the case of sterile powders for the preparation of sterile injectable solutions, the preferred methods of preparation are vacuum-drying and the freeze-drying technique which yields a powder of the active ingredient plus any additional desired ingredient from previously sterile-filtered solution thereof.

For oral therapeutic administration, the compound may be incorporated with excipients and used in the form of ingestible tablets, buccal tablets, troches, capsules, elixirs, suspensions, syrups, wafers, and the like. Compositions or preparations according to the present invention are prepared so that an oral dosage unit form contains compound concentration sufficient to treat a disorder in a subject.

Some examples of substances which can serve as pharmaceutical carriers are sugars, such as lactose, glucose and sucrose; starches such as corn starch and potato starch; cellulose and its derivatives such as sodium carboxymethycellulose, ethylcellulose and cellulose acetates; powdered tragancanth; malt; gelatin; talc; stearic acids; magnesium stearate; calcium sulfate; vegetable oils, such as peanut oils, cotton seed oil, sesame oil, olive oil, corn oil and oil of theobroma; polyols such as propylene glycol, glycerine, sorbitol, manitol, and polyethylene glycol; agar; alginic acids; pyrogen-free water; isotonic saline; and phosphate buffer solution; skim milk powder; as well as other non-toxic compatible substances used in pharmaceutical formulations such as Vitamin C, estrogen and echinacea, for example. Wetting agents and lubricants such as sodium lauryl sulfate, as well as coloring agents, flavoring agents, lubricants, excipients, tableting agents, stabilizers, anti-oxidants and preservatives, can also be present.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

EXAMPLES

The present invention will now be demonstrated using specific examples that are not to be construed as limiting.

General Experimental Procedures

Chemical structures can be elucidated by NMR spectroscopy or in conjunction with mass spectrometry. These methods are known to those in the art.

Example 1

Cell Culture

Cell culture medium is purchased from Invitrogen and fetal bovine serum (FBS) from Hyclone. Cells are propagated and maintained in DMEM medium (high glucose) supplemented with 10% FBS at 37° C. humidified air and 5% $CO_2$.

Example 2

Caspase Assay

Caspase 3/7 Assays.

U2OS cells are plated in solid-white 96-well assay plate ($5 \times 10^3$/well). The same treatment and washout steps as for the cell viability assay are performed. After another 24 h of incubation, caspase 3/7 activity is measured by using Caspase-Glo 3/7 assay (Promega). Caspase-Glo 3/7 reagent is prepared immediately before use by mixing the lysis buffer and luciferase substrate and equilibrated to room temperature. The assay plate is equilibrated to room temperature (~10 min). The same volume of Caspase-Glo 3/7 reagent as culture medium is added to each well (100 µL), the plate is mixed on a plate shaker for ~1 min and incubated at room temperature for 30 min. The luminescence is read in a luminescence plate reader (SpectraMax M5, Molecular Devices, Sunnyvale, Calif.).

Example 3

Cell Viability Assay

Cell Viability Assay.

U2OS cells are seeded in clear-bottom 96-well plates ($5\times10^3$/well), and treated 24 h later with various concentrations of compound (1 nM to 1 µM) or solvent control. 1 h, 4 h, 12 h and 24 h after treatment, culture medium is aspirated, cells rinsed once with fresh medium and wells refilled with fresh medium. After a total of 48 h of incubation, cell viability is measured using MTT according to the manufacturer's instructions (Promega). In parallel, a dose-response analysis is carried out after continuous exposure of cells to compound (48 h). Analogously, other cell types (e.g., colon cancer HCT116) can be used.

Example 4

Compound Activity

In Vitro Translation.

The translation reactions containing 17.5 µL of nuclease-treated rabbit reticulocyte lysate (Promega, Madison, Wis.), 0.5 µL of amino acid mix (minus methionine, 1 mM), 2.0 µL of canine pancreatic microsomal membranes (Promega), 1.0 µL of RNA substrate in nuclease-free water (β-lactamase or α-factor mRNA at 0.1 µg/µL), 1 µL mixture of water and compound or solvent control (0.875 µL water, 0.125 µL of 20 nM, 200 nM, 2 µM, 20 µM, 200 µM, 2 mM compound or solvent control), 1.5-2.0 µL of L-[$^{35}$S]methionine (EasyTag™, 15-20 µCi; PerkinElmer, Waltham, Mass.) and nuclease-free water to a final volume of 25 µL are incubated at 30° C. for 60 min. One reaction without canine pancreatic microsomal membranes is included. 5 µL of the reaction is used for analyzing the results of translation and processing by SDS-PAGE (20%) and autoradiography.

Coupled In Vitro Transcription/Translation.

Human PDGFR-β cDNA plasmid (vector pCMV6-XL5) is obtained from Origene Technologies (Rockville, Md.). In vitro transcription/translation is carried out by using TNT T7 quick coupled transcription/translation systems (Promega). The reactions containing 20 µL of T7 TNT quick master mix, 1 µL of plasmid DNA (1 µg/µL), 1.5 µL canine pancreatic microsomal membranes (Promega), 1 µL mixture of water and compound or solvent control (0.875 µL water, 0.125 µL of 20 nM, 200 nM, 2 µM, 20 µM, 200 µM, 2 mM compound or solvent control), 1.5-2.0 µL of L-[$^{35}$S]methionine (EasyTag™, 15-20 µCi, PerkinElmer) and nuclease-free water to a final volume of 25 µL are incubated at 30° C. for 90 min. One reaction without canine pancreatic microsomal membranes is also included. 5 µL of the reaction is used for analyzing the results of translation and processing by SDS-PAGE (7.5%) and autoradiography.

Protease Protection Assay.

A solution of 1 mg/mL of proteinase K (Roche) in Tris-HCl (pH 7.5) is preincubated at 37° C. for 15 min to degrade contaminating lipases. 9.5 µL of translation reactions are chilled on ice and $CaCl_2$ is added to 10 mM. 1 µL of treated proteinase K is added to the translation reactions (10 µM compound and solvent control) in the presence or absence of 1% Triton X-100. The reactions are incubated at 0° C. for 30 min and stopped by the addition of 2 µL of 50 mM phenylmethylsulfonyl fluoride in ethanol and immediately transferred to boiling SDS-PAGE loading buffer and then analyzed by SDS-PAGE (20%) and autoradiography.

REFERENCES (1) (a) Koehn, F. E.; Carter, G. T. *Nat. Rev. Drug Discov.* 2005, 4, 206-220. (b) Paterson, I.; Anderson, E. A. *Science* 2005, 310, 451-453.

(2) Fenical, W.; Jensen, P. R. *Nat. Chem. Biol.* 2006, 2, 666-673.

(3) Gerwick, W. H.; Tan, L. T.; Sitachitta, N. *Alkaloids Chem. Biol.* 2001, 57, 75-184.

(4) Luesch, H.; Moore, R. E.; Paul, V. J.; Mooberry, S. L.; Corbett, T. H. *J. Nat. Prod.* 2001, 64, 907-910.

(5) (a) Gerwick, W. H.; Proteau, P. J.; Nagle, D. G.; Hamel, E.; Blokhin, A.; Slate, D. L. *J. Org. Chem.* 1994, 59, 1243-1245. (b) Verdier-Pinard, P.; Lai, J.-Y.; Yoo, H.-D.; Yu, J.; Marquez, B.; Nagle, D. G.; Nambu, M.; White, J. D.; Falck, J. R.; Gerwick, W. H.; Day, B. W.; Hamel, E. *Mol. Pharmacol.* 1998, 53, 62-76.

(6) (a) Luesch, H.; Yoshida, W. Y.; Moore, R. E.; Paul, V. J.; Corbett, T. H. *J. Am. Chem. Soc.* 2001, 123, 5418-5423. (b) Luesch, H.; Chanda, S. K.; Raya, M. R.; DeJesus, P. D.; Orth, A. P.; Walker, J. R.; Izpisúa Belmonte, J. C.; Schultz, P. G. *Nat. Chem. Biol.* 2006, 2, 158-167.

(7) Apratoxin A discovery: Luesch et al. *J. Am. Chem. Soc.* 123, 5418-5423 (2001).

(8) Apratoxins B&C discovery: Luesch et al. *Bioorg. Med. Chem.* 10, 1973-1978 (2002)

(9) Apratoxin A/analogue syntheses: Chen & Forsyth *Proc. Natl. Acad. Sci. USA* 101, 12067-12072 (2004) See also: Zhou et al. *Org. Lett.* 5, 3503-3506 (2003); Doi et al. *Org. Lett.* 8, 531-534 (2006); Ma et al. *Chem. Eur. J.* 12, 7615-7626 (2006).

OTHER REFERENCES

Apratoxin D:

Gutiérrez M, Suyama T L, Engene N, Wingerd J S, Matainaho T, and Gerwick W H (2008) Apratoxin D, a potent cytotoxic cyclodepsipeptide from Papua New Guinea collections of the marine cyanobacteria *Lyngbya majuscula* and *Lyngbya sordida. J Nat Prod* 71:1099-1103.

Apratoxin E:

Matthew S, Schupp P J, and Luesch H (2008) Apratoxin E, a cytotoxic peptolide from a Guamanian collection of the marine cyanobacterium *Lyngbya bouillonii. J Nat Prod* 71:1113-1116.

Apratoxin F and G:

Tidgewell, K.; Engene, N.; Byrum, T.; Media, J.; Doi, T.; Valeriote, F. A.; Gerwick, W. H. Evolved diversification of a modular natural product pathway: apratoxins F and G, two cytotoxic cyclic depsipeptides from a Palmyra collection of *Lyngbya bouillonii. ChemBioChem* 2010, 11, 1458-1466.

INCORPORATION BY REFERENCE

The contents of all references (including literature references, issued patents, published patent applications, and co-pending patent applications) cited throughout this application are hereby expressly incorporated herein in their entireties by reference.

EQUIVALENTS

Those skilled in the art will recognize, or be able to ascertain using no more than routine experimentation, many equivalents of the specific embodiments of the invention described herein. Such equivalents are intended with be encompassed by the following claims.

What is claimed:
1. A compound of any of the formulae IX-XII:

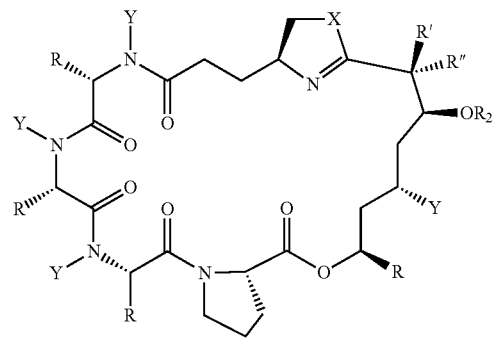

IX

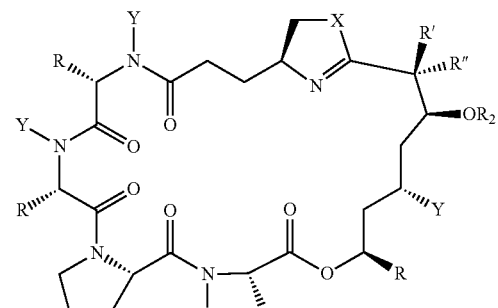

X

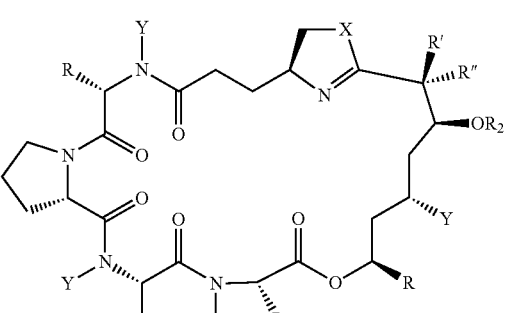

XI

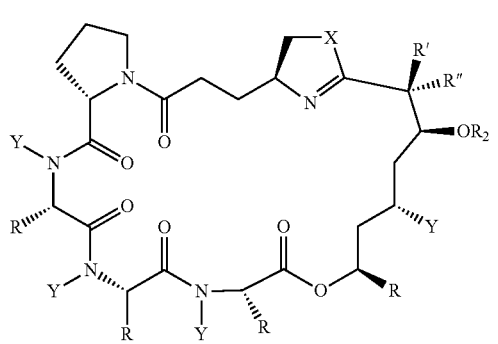

XII wherein
Each X is independently S or O;
Each Y is independently H or Me;
Each R' is independently H or alkyl;
Each R" is independently H or alkyl;

Each R is independently alkyl optionally substituted with OH, OMe, SH, SMe, optionally substituted phenyl, NH$_2$, NH-alkyl, or N(alkyl)(alkyl); or each R is independently the side chain of a naturally-occurring or non-natural amino acid;

or wherein each Y and R and the adjacent atoms attached to them (nitrogen and carbon, respectively) can combine to form a heterocyclic ring;

Each R$_2$ is independently H, alkyl, or —C(O)alkyl.

2. The compound of claim 1, wherein X is S.

3. The compound of claim 1, wherein the compound is one of the following:

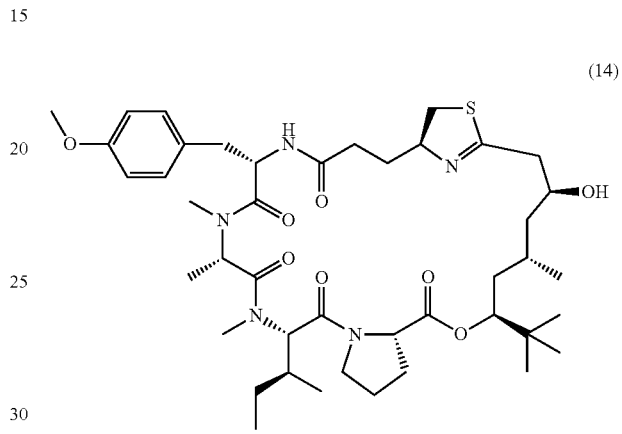

(14)

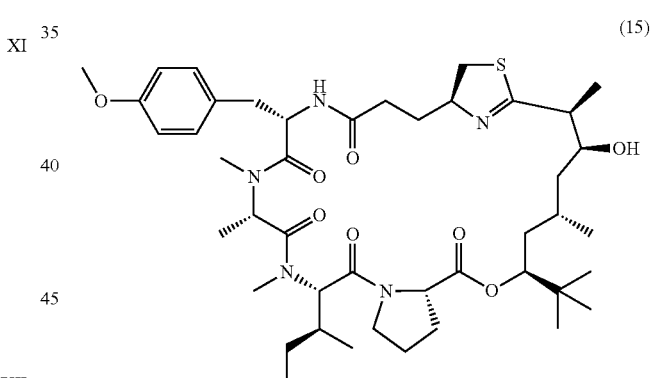

(15)

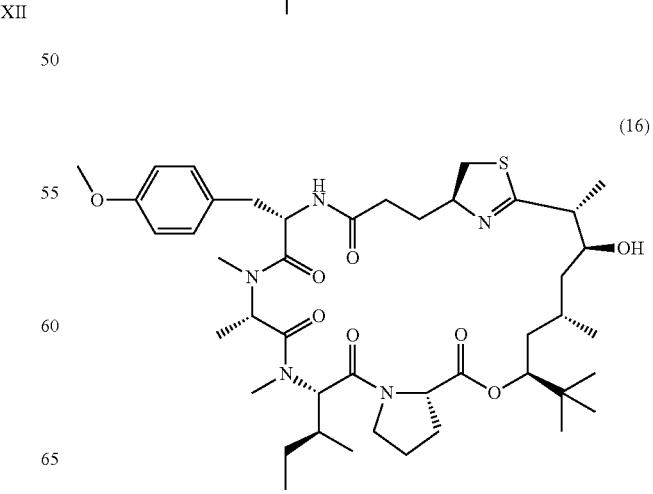

(16)

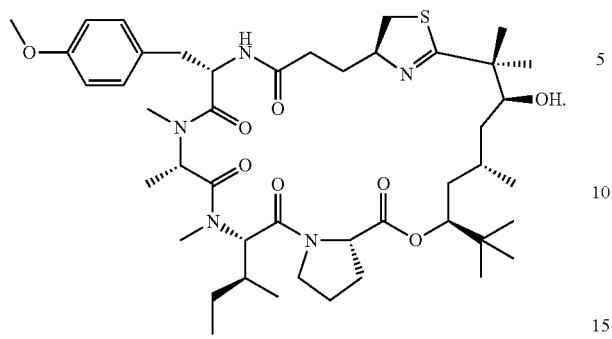
(21)
* * * * *